United States Patent
Carlyle et al.

(10) Patent No.: US 7,722,671 B1
(45) Date of Patent: May 25, 2010

(54) MEDICAL DEVICES WITH ASSOCIATED GROWTH FACTORS

(75) Inventors: Wenda C. Carlyle, Vadnais Heights, MN (US); Sheila J. Kelly, Vadnais Heights, MN (US); Matthew F. Ogle, Saint Paul, MN (US)

(73) Assignee: St. Jude Medical, Inc., St. Paul, MN (US)

( * ) Notice: Subject to any disclaimer, the term of this patent is extended or adjusted under 35 U.S.C. 154(b) by 977 days.

(21) Appl. No.: 09/186,810

(22) Filed: Nov. 5, 1998

Related U.S. Application Data

(63) Continuation-in-part of application No. 09/014,087, filed on Jan. 27, 1998, now abandoned.

(51) Int. Cl.
 *A61F 2/02* (2006.01)
(52) U.S. Cl. ............... 623/11.11; 623/23.72; 424/2.24
(58) Field of Classification Search ............... 623/1.26, 623/2.42; 427/2.24
 See application file for complete search history.

(56) References Cited

U.S. PATENT DOCUMENTS

| | | | |
|---|---|---|---|
| 3,755,042 A * | 8/1973 | Robertson et al. ........... 156/245 |
| 4,648,881 A * | 3/1987 | Carpentier et al. |
| 4,786,287 A | 11/1988 | Nashef et al. ................ 8/94.21 |
| 4,798,611 A | 1/1989 | Freeman, Jr. ................ 623/11 |
| 4,828,563 A * | 5/1989 | Muller-Lierheim ....... 623/23.63 |
| 5,002,582 A | 3/1991 | Guire et al. ................... 623/11 |
| 5,147,400 A | 9/1992 | Kaplan et al. ................ 623/11 |
| 5,147,514 A | 9/1992 | Mechanic ............... 204/157.68 |
| 5,192,312 A | 3/1993 | Orton ........................... 623/11 |
| 5,194,596 A | 3/1993 | Tischer et al. ............... 530/399 |
| 5,263,992 A * | 11/1993 | Guire .......................... 623/66 |
| 5,308,641 A * | 5/1994 | Cahalan et al. ................ 427/2 |
| 5,606,026 A * | 2/1997 | Rodman ................... 530/387.9 |
| 5,607,918 A | 3/1997 | Eriksson et al. ............... 514/12 |
| 5,613,982 A * | 3/1997 | Goldstein ................ 623/23.76 |
| 5,672,508 A * | 9/1997 | Gyuris et al. ............ 435/320.1 |
| 6,033,719 A * | 3/2000 | Keogh ........................ 427/2.12 |
| 6,099,563 A * | 8/2000 | Zhong ........................ 623/1.46 |
| 6,150,515 A * | 11/2000 | Sharp et al. ................ 536/23.5 |

(Continued)

FOREIGN PATENT DOCUMENTS

EP  0 476 983 A1  3/1992

(Continued)

OTHER PUBLICATIONS

Weaterford et al., Vascular endothelial growth factor and heprin in a biologic glue promotes human aortic endothelial cell proliferation with aortic smmoth muscle cell inhibition., Surgery, 120, 2, Aug. 1996.*

(Continued)

*Primary Examiner*—Paul Prebilic
(74) *Attorney, Agent, or Firm*—Hallie A. Finucane; Westman, Champlin & Kelly, P.A.

(57) ABSTRACT

A polypeptide growth factor is associated with a substrate to promote population of the substrate with endothelial cells. In a preferred approach, the growth factor is associated with the substrate by crosslinking under suitably mild conditions such that the growth factor is active following the crosslinking process. Thus, a prosthesis is formed with growth factor crosslinked to the substrate.

24 Claims, 7 Drawing Sheets

Calcium Content of Leaflets
(mg calcium / gm tissue dry weight)

U.S. PATENT DOCUMENTS 6,497,729 B1 * 12/2002 Moussy et al. ........... 623/23.57

FOREIGN PATENT DOCUMENTS

| EP | 0 506 477 A1 | 9/1992 |
| EP | 0 550 296 A2 | 7/1993 |
| EP | 0 742 020 A2 | 11/1996 |
| WO | WO 86/00526 | 1/1986 |
| WO | WO 95/24473 | 9/1995 |
| WO | WO-98/00695 * | 1/1998 |

OTHER PUBLICATIONS

"Accelerated Endothelialization by Local Delivery of Recombinant Human Vascular Endothelial Growth Factor Reduces In-Stent Intimal Formation" by, Bell et al., Biochemical and Bio Physical Research Communication 235, 311-316 (1997).

"Conditional Switching of Vascular Endothelial Growth Factor (VEGF) Expression in Tumors: Induction of Endothelial Cell Shedding and Regression of Hemangioblastoma-like Vessels by VEGF Withdrawal" by, Benjamin et al., Proc. Natl. Acad. Sci. USA, vol. 94. pp. 8761-8766, Aug. 1997, Medical Sciences.

"Passivation of Metallic Stents After Arterial Gene Transfer of phVEGF$_{ics}$Inhibits Thrombus Formation and Intimal Thickening" by, VanBelle et al., JACC vol. 29. No. 6. May 1997:1371-1379.

"Stent Endothelialization: Time Course, Impact of Local Catheter Deliver, Feasibility of Recombinant Protein Administration, and Response Lo Cytokine Expedition" by, Van Balle et al., Circulation, vol. 95. No. 2 Jan. 21, 1997, pp. 438-448.

"Stimulation of Endothelial Cell Migration by Vascular Permeability Factor/Vascular Endothelial Growth Factor through Cooperative Mechanisms Involving the $\alpha_r\beta_{J}$, Integrin. Osteopontin, and Thrombin" by, Senger et al., American Journal of Pathology, vol. 149, No. 1, Jul. 1996, 293-305.

"Synergistic Effect of Vascular Endothelial Growth Factor and Basic Fibroblast Growwth Factor on Angiogenesis in Vivo" by, Asahara et al., Supplemental II Circulation vol. 92, No. 9, Nov. 1, 1995, pp. 365-371.

"Vascular Endothelial Growth Factor Inhibites Endothelial Cell Apoptosis Induced by Tumor Necrosis Factor $\alpha$: Balance Between Growth and Death Signals" by, Spyridopoulos et al., J. Mol. Cell. Cardiol., vol. 29, 1321-1330 (1997).

"Vascular Permeability Factor/Vascular Endothelial Growth Factor Inhibits Anchorage-Disruption-Induced Apoptosis in Microvessel Endothelial Cells by Inducing Scaffold Formation", by Watanabe et al., Experimental Cell Research 233, pp. 340-349 (1997).

"Vascular Permeability Factor/Vascular Endothelial Growth Factor (VPF/VEGF) Delays and Induces Escape from Senescence in Human Dermal Microvascular Endothelial Cells", by Watanabe et al., Oncogene (1997) 14, 2025-2032.

* cited by examiner

Figure 4
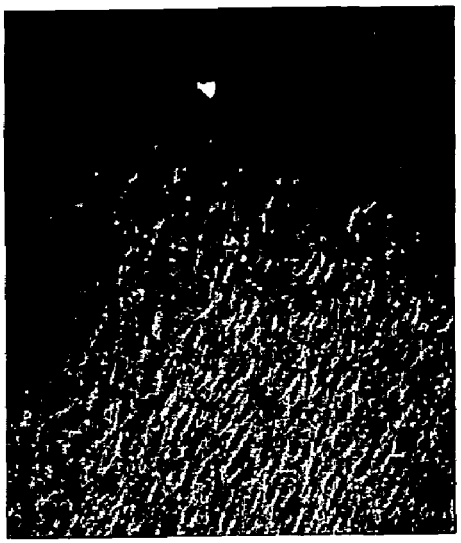
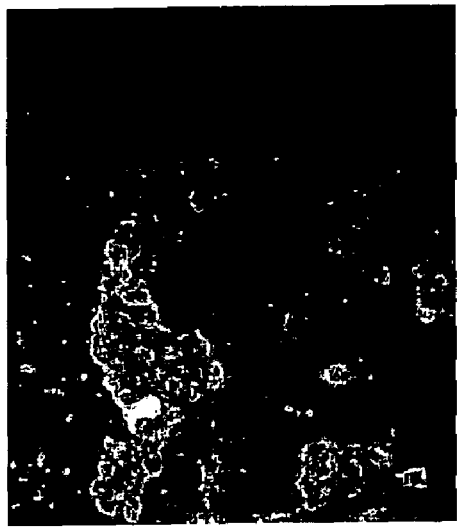
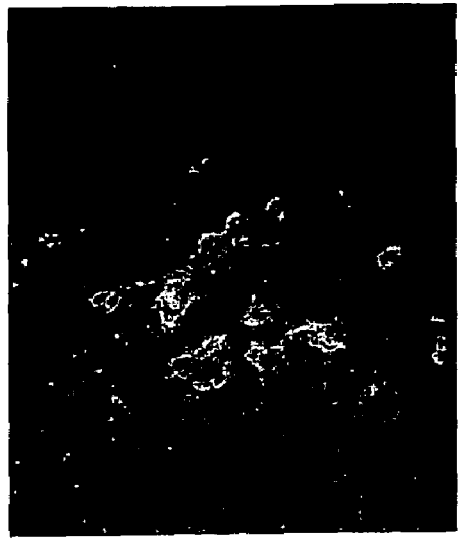

Figure 7: Calcium Content of Leaflets
(mg calcium / gm tissue dry weight)

Figure 8
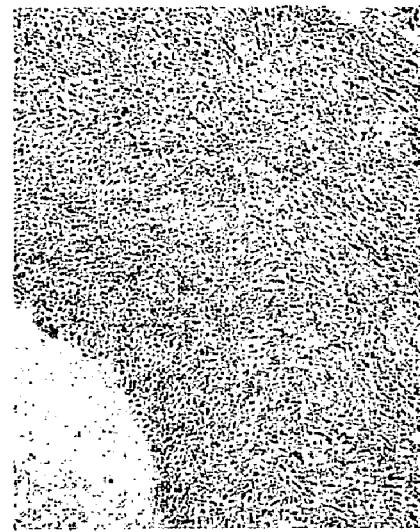
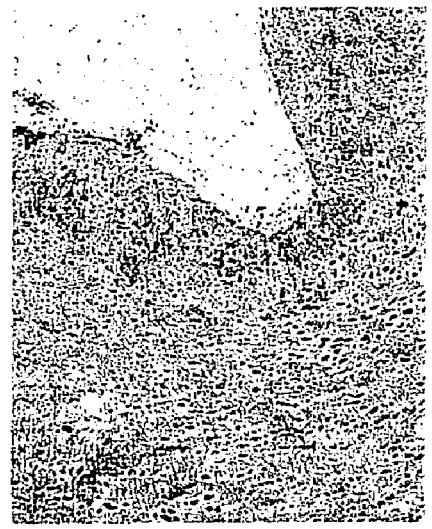

MEDICAL DEVICES WITH ASSOCIATED GROWTH FACTORS

CROSS REFERENCE TO RELATED APPLICATIONS

This application is a Continuation-In-Part of U.S. application Ser. No. 09/014,087, filed on Jan. 27, 1998, entitled "PROSTHESES WITH ASSOCIATED GROWTH FACTORS," (now abandoned) which is incorporated herein by reference.

FIELD OF THE INVENTION

The invention relates to prostheses having components that have been modified with a polypeptide growth factor. The invention further relates to methods for producing these prostheses.

BACKGROUND OF THE INVENTION

Prostheses, i.e., prosthetic devices, are used to repair or replace damaged or diseased organs, tissues and other structures in humans and animals. Prostheses must be generally biocompatible since they are typically implanted for extended periods of time. For example, prostheses can include artificial hearts, artificial heart valves, ligament repair material, vessel repair, surgical patches constructed of mammalian tissue and the like.

Prostheses can be constructed from natural materials such as tissue, synthetic materials or a combination thereof. For example, synthetic prostheses such as mechanical heart valve prostheses are manufactured from biocompatible metals and other materials such as graphite and polyester. Although mechanical heart valves have the advantage of proven durability through decades of use, they are associated with a high incidence of blood clotting on or around the prosthetic valve. Blood clotting can lead to acute or subacute closure of the valve or associated blood vessel. For this reason, patients with implanted mechanical heart valves remain on anticoagulants for as long as the valve remains implanted. Anticoagulants impart a 3-5% annual risk of significant bleeding and cannot be taken safely by certain individuals.

Besides mechanical heart valves, heart valve prostheses can be constructed with tissue leaflets or polymer leaflets. Thrombosis and subsequent calcification are concerns associated with polymer heart valves. Calcification of these valves can lead to failure.

Prosthetic tissue heart valves can be derived from, for example, porcine heart valves or manufactured from other biological material such as bovine pericardium. Biological materials in prosthetic heart valves generally have profile and surface characteristics that generally provide laminar, non-turbulent blood flow. Therefore, intravascular clotting is less likely to occur than with mechanical heart valves. Unfortunately, prosthetic tissue heart valves are limited by a tendency to fail beginning about seven years following implantation. Valve degeneration is particularly rapid in young patients and during pregnancy.

Calcification, i.e., the deposition of calcium salts, especially calcium phosphate (hydroxyapatite), appears to be a major cause of degeneration. Efforts to address the calcification problem have included treating glutaraldehyde-fixed valve prostheses with compounds to reduce calcium nucleation. Other approaches include use of alternative tissue fixation techniques since evidence suggests that glutaraldehyde fixation can contribute to calcification and mechanical degradation. In addition, since nonviable cells can be sites for calcium deposition, various processes have been developed to remove nonviable cells while leaving the extracellular matrix intact. Intact tissue with viable cells has natural protection against calcification.

Another major disadvantage of tissue based prostheses is the failure of such devices to be self-maintaining. Long term durability is affected by the ability of viable cells to populate the implanted tissue and to carry out maintenance functions. The importance of viable cells has been studied in the context of homograft transplants, i.e., transplants from one member of a species to another member of the same species. Proper homograft preservation can maximize the number of viable cells remaining in the tissue as determined by matrix protein synthesis. Preservation techniques that do not promote cell survival, such as long term storage at 4° C., are associated with reduced in vivo durability and increased reoperation rates.

SUMMARY OF THE INVENTION

In a first aspect, the invention pertains to a prosthesis comprising a substrate and a polypeptide growth factor crosslinked to said substrate, the polypeptide growth factor being effective to stimulate the association of viable cells with the substrate.

In another aspect, the invention pertains to a method for producing a biocompatible material, the method comprising:
  crosslinking a polypeptide growth factor to a substrate under conditions such that the polypeptide growth factor is effective to stimulate the association of viable cells with the substrate.

BRIEF DESCRIPTION OF THE DRAWINGS

FIG. 4 is a set of micrographs of human aortic endothelial cells colonizing glutaraldehyde crosslinked porcine aortic valve leaflet tissue (FIG. 4A), glutaraldehyde crosslinked tissue treated with ethanol (FIG. 4B), or glutaraldehyde crosslinked tissue treated with ethanol and then with a solution of 100 ng/ml VEGF+0.01% glutaraldehyde. The cells were visualized by fluorescent labeling.

FIG. 8 is a set of micrographs of glutaraldehyde crosslinked porcine aortic valve leaflet tissue that received either no further treatment (FIG. 8A), ethanol treatment (FIG. 8B) or ethanol and VEGF treatment (FIG. 8C) prior to subcutaneous implantation in juvenile male rats for 21 days. With the staining system used, calcium phosphate stains brown and is depicted as small dark patches in the photographs.

DETAILED DESCRIPTION OF THE PREFERRED EMBODIMENTS

Figure 1:
FIG. 1 is a micrograph of a crosslinked tissue sample that was treated with VEGF prior to a five day incubation period during which the tissue was in contact with viable endothelial cells grown on an insert within a tissue culture well. Endothelial cells present on the fixed tissue are visualized by fluorescent labeling.

A polypeptide growth factor or a fragment thereof can be associated with a tissue substrate or a synthetic substrate in vitro. Generally, the substrate forms, or will form, all or a portion of a prosthesis. Preferred polypeptide growth factors include vascular endothelial growth factor (VEGF) and related compounds. Following modification of the substrate with VEGF, the VEGF can stimulate endothelial cell chemotaxis and proliferation. In preferred embodiments, the substrate is fixed. The association of viable endothelial cells with the prosthetic tissue should contribute to the long term viability of the prosthesis. VEGF modification is particularly suitable for the production of prostheses that naturally have an endothelial or epithelial cell lining, such as vascular components, cardiovascular structures, portions of the lymphatic system, uterine tissue or retinal tissue.

The VEGF can be associated with the substrate in a variety of ways. For example, the substrate can be combined with a VEGF solution such that the VEGF becomes joined with the prosthetic tissue by direct attachment. Alternatively, the VEGF can be associated with the prosthetic tissue using an adhesive. In addition, the VEGF can be joined with the prosthetic tissue using chemical bonding.

As demonstrated in Example 1 below, direct attachment or association can occur by addition of VEGF to crosslinked tissue. While the mechanism of direct attachment of the VEGF with the crosslinked tissue is unknown, the VEGF may bind with free glutaraldehyde functional groups in the crosslinked tissue.

With respect to chemical bonding of the VEGF to the tissue, VEGF can be crosslinked to the tissue with glutaraldehyde. The conditions for crosslinking VEGF to the tissue must be carefully controlled to maintain desired levels of VEGF activity following the crosslinking and to prevent residual glutaraldehyde mediated cytotoxicity. The controlled crosslinking of VEGF to the tissue with glutaraldehyde can effectively adhere VEGF to either crosslinked or uncrosslinked tissue. Thus, this approach is particularly appropriate to associate VEGF with uncrosslinked autograft or homograft tissue.

VEGF can effectively induce the growth of endothelial cells on the substrate in vitro or in vivo such that the tissue becomes populated with viable cells. For in vivo growth, the substrate with associated VEGF can be implanted into a patient. Once implanted in the patient, endothelial cells are attracted to the prosthesis due to the presence of VEGF. Alternatively, endothelial cells can be associated with the prosthesis in a cell culture system, as described below.

A. Prostheses

Prostheses can include a tissue substrate or a synthetic substrate, at least as a component, such that the substrate is suitable as a location for cellular attachment. Generally, these prostheses are designed for implantation into a patient for extended periods of time. Prostheses include, for example, artificial hearts, artificial heart valves, annuloplasty rings, vascular and structural stents, vascular grafts, pledgets, suture, leads, permanently in-dwelling percutaneous devices, vascular or cardiovascular shunts, dermal grafts for wound healing, and surgical patches. Biomedical devices that are designed to dwell for extended periods of time within a patient are also suitable to include substrates with associated growth factors. These devices include, for example, Hickman catheters.

Natural tissues for use as substrates are derived from an animal species, typically mammalian, such as human, bovine, porcine, canine, seal or kangaroo. These tissues can be obtained from, for example, heart valves, aortic roots, aortic walls, aortic leaflets, pericardial tissue such as pericardial patches, connective tissue such as dura mater, bypass grafts, tendons, ligaments, skin patches, blood vessels, human umbilical tissue, bone, fascia, submucosa and the like. These natural tissues generally include collagen-containing material. Natural tissue is typically, but not necessarily, soft tissue. A tissue-based prosthesis can maintain structural elements from its native form, and/or structural elements can be incorporated into the prosthesis from the assembly of distinct pieces of tissue. For example, a heart valve prosthesis can be assembled from a porcine heart valve, from bovine pericardium or from a combination thereof.

Synthetic substrates can be formed from synthetic polymers and/or biological polymers, such as those generally found in a natural tissue matrix, to form a synthetic tissue matrix. In particular, collagen and elastin polymers can be formed into a matrix corresponding to a tissue component by any of a variety of techniques such as weaving and molding. The synthetic substrate formed from these biological polymers mimic a natural tissue matrix. Alternatively, synthetic substrates can be in the form of a synthetic tissue with a matrix including synthetic and/or biological polymers along with viable and/or non-viable cells. The polymers can be, but are not necessarily, bioresorbable. Suitable synthetic and biological polymers are described below.

Tissues can be fixed by crosslinking. This provides mechanical stabilization, for example, by preventing enzymatic degradation of the tissue. Crosslinking also removes antigenic sites that could result in the patient's rejection of the prosthesis. Glutaraldehyde or formaldehyde typically is used for fixation, but other fixatives can be used, such as epoxides and other difunctional aldehydes. Xenografts, i.e., prostheses incorporating tissue from a species different from the patient's species, generally are fixed prior to use. Homografts, i.e., prostheses incorporating tissue of a different individual of the patient's species, may or may not be fixed prior to use. Similarly, autografts, i.e., prostheses incorporating tissue from the same individual, may or may not be fixed prior to use.

The prostheses can include other non-tissue components such as polymeric material, ceramics and metal. Appropriate ceramics include, without limitation, hydroxyapatite, alumina and pyrolytic carbon. Polymeric materials can be fabricated from synthetic polymers as well as purified biological polymers. Appropriate synthetic materials may include hydrogels and other synthetic materials that cannot withstand severe dehydration.

Appropriate synthetic polymers include without limitation polyamides (e.g., nylon), polyesters, polystyrenes, polyacrylates, vinyl polymers (e.g., polyethylene, polytetrafluoroethylene, polypropylene and poly vinyl chloride), polycarbonates, polyurethanes, poly dimethyl siloxanes, cellulose acetates, polymethyl methacrylates, ethylene vinyl acetates, polysulfones, nitrocelluloses and similar copolymers. Bioresorbable polymers can also be used such as dextran, hydroxyethyl starch, gelatin, derivatives of gelatin, polyvinylpyrolidone, polyvinyl alcohol, poly[N-(2-hydroxypropyl) methacrylamide], poly(hydroxy acids), poly(epsilon-caprolactone), polylactic acid, polyglycolic acid, poly (dimethyl glycolic acid), poly(hydroxy buterate), and similar copolymers. These synthetic polymeric materials can be woven into a mesh to form a matrix or substrate. Alternatively, the synthetic polymer materials can be molded or cast into appropriate forms.

Biological polymers can be naturally occurring or produced in vitro by, for example, fermentation and the like. Purified biological polymers can be appropriately formed into a substrate by techniques such as weaving, knitting, casting, molding, extrusion, cellular alignment and magnetic alignment. For a description of magnetic alignments see, for example, R. T. Tranquillo et al., Biomaterials 17:349-357 (1996), incorporated herein by reference. Suitable biological polymers include, without limitation, collagen, elastin, silk, keratin, gelatin, polyamino acids, cat gut sutures, polysaccharides (e.g., cellulose and starch) and copolymers thereof.

B. Vascular Endothelial Growth Factor (VEGF)

VEGF refers to a family of polypeptides that have been found to preferentially stimulate growth of vascular endothelial cells over other cells, such as smooth muscle cells. Several forms of VEGF have been identified. VEGF polypeptides generally have sequence homology with platelet-derived growth factor, which can alter the migration and proliferation of a variety of cell types. VEGF occasionally has been referred to as vascular permeability factor.

The originally identified form of VEGF has a molecular weight of about 45 to 46 kilodaltons (kDa). This form apparently is a homodimer with each subunit having a molecular weight of about 23 kDa. The c-DNA sequences encoding the human polypeptide (165-amino acids, $hVEGF_{165}$) and the corresponding bovine polypeptide (164-amino acids, $bVEGF_{164}$) have been determined. In addition, variants of the polypeptides with 121-amino acids for the human version ($hVEGF_{121}$) and 120-amino acids for the bovine version ($bVEGF_{120}$) also have been identified. For the corresponding amino acid sequences, see U.S. Pat. No. 5,194,596, to Tischer et al., incorporated herein by reference. Other insoluble variants have been identified with 189 and 206-amino acids, respectively. See, for example, E. Tischer et al., "The human gene for vascular endothelial growth factor. Multiple protein forms are encoded through alternative exon splicing," J. Biol. Chem. 266:11947-11954 (1991) and K. A. Houck et al., "The vascular endothelial growth factor family: identification of a fourth molecular species and characterization of alternative splicing of RNA," Molec. Endocrinology 5:1806-1814 (1991), both incorporated herein by reference.

Another form of VEGF, entitled VEGF II, is a heterodimer. As isolated from rat glioma cells, the first subunit has 190- amino acids while the second subunit has a 135-amino acid form and an 115-amino acid form. VEGF II is described in EP 0 476 983A, incorporated herein by reference.

A single polypeptide human VEGF, unnamed, also has been identified. This polypeptide has a molecular weight of roughly 80 kDa. The corresponding cDNA was isolated and a 728-amino sequence was determined from the cDNA sequence. Details of the protein are provided in EP 0 550 296A, incorporated herein by reference.

Still another human growth factor, VEGF2, has been identified from early stage human embryo osteoclastomas, adult heart and several breast cancer lines. VEGF2 has 350 amino acids, of which about 24 amino acids represent a leader sequence. The sequence for VEGF2 is disclosed in WO 95/24473, incorporated herein by reference.

Recently, VEGF-B, another variant of VEGF, has been identified. VEGF-B appears to be associated with heart and skeletal muscles. Full sequences for mouse and human VEGF-B are presented in U.S. Pat. No. 5,607,918, to Eriksson et al., incorporated herein by reference.

In addition to VEGF variants that are expressed in mammalian cells under normal physiological conditions, viral proteins such as the Tat protein from human immuno-deficiency virus (HIV)-1 share sequence homology with VEGF and bind to native VEGF receptors. These properties are described in Albini et al., "The angiogenesis induced by HIV-1 Tat protein is mediated by the Flk-1/KDR receptor on vascular endothelial cells," Nature Medicine 2(12):1371-1375 (1996) and Mitola et al., "Tat-human immunodeficiency virus-1 induces human monocyte chemotaxis by activation of vascular endothelial growth factor receptor-1," Blood 90(4): 1365-1372 (1997), both of which are incorporated herein by reference. Through an interaction with these VEGF receptors, a Tat protein stimulates endothelial cell chemotaxis and proliferation. Thus, for the purposes of this application, the Tat protein and other similar viral proteins that bind VEGF receptors are considered a VEGF growth factor.

As described above, a variety of VEGF polypeptides have been identified. Many of these are associated with particular tissues. At least some of the polypeptides have variations based on alternative message splicing, such as $hVEGF_{165}$ and $hVEGF_{121}$. As used in the other sections of this application, "VEGF" refers, without limitation, to all previously identified VEGF polypeptides, such as those described in this section, as well as any future identified VEGF polypeptides, that selectively promote the chemotaxis or proliferation of endothelial cells. "VEGF" also refers to polypeptide fragments that maintain their ability to selectively promote the chemotaxis or proliferation of endothelial cells. As noted above, for example, human $VEGF_{121}$ is a naturally occurring fragment of human $VEGF_{165}$. Recombinant human $VEGF_{165}$, human $VEGF_{121}$, and mouse VEGF are available from R&D Systems of Minneapolis, Minn. Similarly, "VEGF" referred to herein includes VEGF proteins modified by chemical additions to the protein molecule by covalent or noncovalent binding.

Using standard molecular biology techniques (see, for example, Sambrook, Fritsch and Maniatis, "Molecular Cloning: A Laboratory Manual," 2nd edition, Cold Spring Harbor Press, (1989)), it is possible to make recombinant modified forms of natural VEGF polypeptides. These straightforward modifications include addition of amino acids on the N-terminus, the C-terminus or both. Also, modifications can be made by substituting amino acids along the polypeptide chain. Some modifications may destroy activity of the protein. It is straightforward to eliminate inactivating modifications by testing for activity in cell culture systems. Active forms of these modified polypeptides are within our general definition of "VEGF."

C. Joining of VEGF with a Substrate

The joining of VEGF with a substrate can involve direct attachment, application of a coating including an adhesive, or chemical binding. VEGF may be joined with only a portion of a substrate or the entire substrate. If VEGF is bound to a portion of the substrate, cells may still associate with other portions of the substrate not bound with VEGF as a result of the VEGF being present on part of the substrate.

Direct attachment entails combining the substrate, such as a tissue substrate, with a solution of the VEGF. In particular, it has been discovered that the VEGF can associate with glutaraldehyde crosslinked biological tissue such that the VEGF is not easily washed off. This direct attachment is particularly effective when the tissue has been incubated in 0.5% glutaraldehyde for less than one month prior to incubation with VEGF. The subsequent binding of the VEGF to glutaraldehyde crosslinked tissue seems to last for at least moderate periods of time, up to a month or longer, when the tissue is in contact with a buffer solution. Evidence has been obtained, as set forth in Example 1 below, that treatment with ethanol prior to contact with VEGF reduces the association of VEGF with fixed tissue. The reduction of the association of VEGF resulting from incubating the tissue with ethanol possibly could be due to elimination of VEGF binding sites, inactivation of VEGF binding sites or binding of ethanol at VEGF binding sites.

For direct attachment of VEGF to a substrate, such as a glutaraldehyde crosslinked tissue, the substrate or a portion thereof is combined with a solution of VEGF at a concentration generally from about 1 ng/ml to about 1 µg/ml and preferably from about 25 ng/ml to about 250 ng/ml. During incubation with the VEGF, the solution preferably is cooled, for example, to about 4° C. The substrate preferably remains in the VEGF solution at about 4° C. for about 24 hours and up to about 14 days or more. The VEGF solution preferably is buffered at a pH ranging from about 6 to about 8.5, and more preferably ranging from about 6.3 to about 7.4. Suitable buffers can be based on, for example, the following compounds: phosphate, borate, bicarbonate, carbonate, cacodylate, citrate, and other organic buffers such as tris(hydroxymethyl) aminomethane (TRIS), N-(2-hydroxyethyl)piperazine-N'-(2-ethanesulfonic acid) (HEPES), and morpholine propanesulphonic acid (MOPS).

Alternatively, VEGF can be associated with the substrate through the use of a binder or adhesive. The VEGF and the adhesive form a coating on the substrate. Preferred adhesives include, for example, biologic glues such as fibrin glue, and the like. Fibrin glue can be formed from the polymerization of fibrinogen and thrombin. Suitable fibrin glues are available from, for example, Immuno AG, Austria and Zymogenetics, Seattle, Wash.

To apply the VEGF with a fibrin glue, a small amount of thrombin can be absorbed to the substrate. VEGF can be mixed with a solution containing fibrinogen to yield a solution with a VEGF concentration preferably ranging from about 1 ng/ml-10 µg/ml. Then, the fibrinogen/VEGF mixture can be brushed over the surface of the substrate with absorbed thrombin, or the tissue with absorbed thrombin can be dipped into the fibrinogen/VEGF solution. The VEGF-adhesive coating can be applied to all or just a portion of the substrate. With synthetic substrates, the VEGF also can be incorporated into the substrate material when the substrate is formed.

Fibrin glues and similar glues are resorbed slowly by the patient following application. VEGF can be mixed with other resorbable polymers and formed into a coating on a substrate. Suitable resorbable polymers include, for example, dextran, hydroethyl starch, gelatin, derivatives of gelatin, polyvinylpyrrolidone, polyvinylalcohol, poly[N-(2-hydroxylpropyl) methacrylamide], polyglycols, polyesters, poly (orthoesters), poly(ester amides), polyanhydrides. Resorbable polyesters include, for example, poly (hydroxy acids) and copolymers thereof, poly(ε-caprolactone), poly (dimethyl glycolic acid), and poly (hydroxy butyrate). Preferred resorbable polymers include, for example, D, L-polylactic acid, L-polylactic acid, poly(glycolic acid), and copolymers of L-lactic acid, D-lactic acid and glycolic acid. Furthermore, the VEGF can be stored in interstices of a polymer matrix. The polymer matrix can be resorbable to release the VEGF material or have appropriate porosity such that the VEGF can gradually diffuse out of the substrate.

The various approaches based on natural or synthetic bioresorbable polymers have the advantage of establishing a concentration gradient of VEGF such that the VEGF can act as a chemotactic agent signaling cells to migrate toward a higher concentration of VEGF. Also, a more precise dose can be delivered over a limited period of time.

In other embodiments, the association of VEGF with the substrate involves chemical binding. Chemical binding includes, for example, covalent bonding, a plurality of non-covalent chemical interactions or both covalent and noncovalent interactions. Noncovalent chemical interactions include, for example, hydrogen bonding, van der Waals interactions, ionic interactions and molecular rearrangements, which characterize, for example, antibody-antigen, specific binding protein-receptor and enzyme-substrate associations. In other words, reactants or binding agents are used to form a direct chemical interaction between the VEGF and the substrate, possibly involving a linker molecule. The chemical binding of the VEGF preferably takes place at or near physiological pH, preferably ranging from about 6 to about 8.5 and more preferably from about 6.3 to about 7.4.

The chemical binding of VEGF can involve covalent bonding to the surface of the substrate with reactive agents such as glutaraldehyde and other general crosslinking agents. A typical procedure for chemical binding of VEGF to the surface of a tissue makes use of glutaraldehyde, which crosslinks proteins by way of two aldehyde groups. Since glutaraldehyde is typically used for fixation of some biocompatible materials, the non-specific crosslinking to bind the VEGF to the biocompatible material can be performed simultaneously with fixation of the tissue. Alternatively, the non-specific crosslinking to covalently bond the VEGF can be performed as a separate step before or after the completion of a fixation process, assuming a fixation step is performed. Other chemical reagents for covalent bonding of VEGF to a substrate include, for example, epoxies.

Preferably, the binding of VEGF to a substrate with a crosslinking agent is performed under carefully controlled conditions to avoid inactivating the VEGF. In particular, the crosslinking is preferably performed with a dilute solution of crosslinking agent, such as glutaraldehyde. Crosslinking preferably is performed with a concentration of crosslinking agent less than about 0.1% crosslinking agent, preferably less than about 0.05% crosslinking agent and more preferably from about 0.005% to about 0.02% crosslinking agent. According to conventional use in the field, percent values are based on a volume per volume dilution of a concentrated volume percent stock solution, generally a 50 percent by volume stock solution.

The crosslinking can be performed for at least about 5 minutes and generally is performed for about 15 minutes to about 24 hours or longer. In particular, the crosslinking of VEGF to the substrate can be performed preferably for less than about 1 hour and, more preferably, for between about 15 minutes and about 30 minutes. It has been observed that the extent of VEGF binding, as evidenced by VEGF's ability to stimulate endothelial cell proliferation in vitro, levels off relatively quickly with respect to crosslinking time. Preferred crosslinking times can be evaluated empirically based on the disclosure herein.

Under the preferred mild conditions described herein, the tissue generally is not significantly fixed. If desired, a size exclusion membrane, such as dialysis tubing, can be used during the simultaneous incubation of VEGF and glutaraldehyde. For example, dialysis tubing with a 10,000 molecular weight cutoff can be used to contain the substrate and the VEGF solution in a relatively small volume. The tubing with the substrate and the VEGF can be immersed in a dilute solution of glutaraldehyde. The glutaraldehyde can permeate the dialysis tubing, but the VEGF solution remains inside the tubing due to its larger molecular size. This procedure allows for the use of a small volume of VEGF and a relatively larger volume of crosslinking solution.

On the other hand, chemical binding of VEGF to the substrate can involve specific binding interactions. If selected accordingly, the specific binding interactions can be used to target specific locations within the substrate. The targeting of specific locations can be useful, for example, if specific locations are resistant to colonization by endothelial cells or if colonization by endothelial cells is particularly beneficial at specific locations. An example of a possible target location would be the leaflets of a heart valve prosthesis.

One method of targeting a particular location involves the use of linkers that target specific cellular or extracellular binding sites within a natural tissue. In certain embodiments, the linker is covalently bound to the VEGF molecule, and the linker associates with the tissue by a plurality of non-covalent interactions. Alternatively, the linker can be covalently bound to the tissue and the VEGF can be associated with the linker by a plurality of non-covalent interactions. A variety of commercially available antibodies and other specific binding reagents may be used as linkers. Alternatively, antibodies can be prepared by conventional techniques.

A VEGF polypeptide having an attached antibody or any other comparable targeting molecule or an engineered chimera of the VEGF polypeptide and the targeting molecule is considered a VEGF molecule for the purposes of the present application. The chemical binding of compounds to antibodies as well as the development of chimeras is well established, especially where the compound is a protein. Empirical adjustments can be made to ensure that the activity of the VEGF molecule is not significantly impaired.

In an alternative embodiment, photochemical coupling can be used for covalent coupling. Photochemical coupling is based on the use of high energy light, e.g., ultraviolet light, to form reactive intermediates of certain functional groups. These reactive intermediates can form carbon-carbon bonds between two compositions. Aryl ketone functional groups are particularly useful in this respect.

Photochemical coupling can be used for attachment of VEGF to tissue. See, for example, Dunkirk et al., J. Biomaterials Applications 6:131-156 (1991), incorporated herein by reference. The tissue may or may not be separately crosslinked since the photochemical coupling generally also crosslinks the tissue, i.e., photofixation. Alternatively, photochemical coupling can be used to attach a linker to the tissue either before, after, or during binding of the linker to the VEGF polypeptide.

Regardless of the nature of the interaction, the bound VEGF generally is in equilibrium with unbound molecules. As a result, the VEGF may eventually be lost to the surrounding solution if the solution is replenished. For some applications it may be sufficient for the VEGF to be bound for a relatively short period of time, such as hours or days, if sufficient viable endothelial cells proliferate on the tissue during the relevant time. In other circumstances, it may be desirable for longer term binding of the VEGF to the tissue, such as months or years. The nature of the association of the VEGF with the tissue can be selected accordingly.

D. Other Modifiers

It may be desirable to associate other molecules with the substrate, in addition to VEGF, to improve the substrate's performance in a prosthesis. Endothelialization due to joining of VEGF with the substrate may reduce the incidence of calcification and infection. Nevertheless, since calcification is a major mode of failure for bioprosthetic tissue, VEGF can be used in conjunction with a biocompatible anti-calcification treatment. Thus, it may be desirable to include agents that act to further reduce calcification and/or microbial infection.

Ethanol is a proven anticalcification treatment, as described in Vyavahare et al., Circulation 95:479-488 (1997), incorporated herein by reference, and in U.S. Pat. No. 5,746,775 to Levy et al., incorporated herein by reference. Used together, ethanol and VEGF can facilitate the production of a long-term viable tissue with ethanol retarding early onset calcification and VEGF stimulating a viable endothelial layer. Example 4 demonstrates the ability of ethanol treatment to inhibit calcification of glutaraldehyde crosslinked porcine aortic valve leaflets in a juvenile rat subcutaneous implant model. This Example also shows that treatment of these leaflets with VEGF, in addition to ethanol, can further attenuate calcification. In addition, aluminum, iron and magnesium ions have been found to reduce calcification. These polyvalent ions can be directly associated with tissue as described in U.S. Pat. No. 5,094,661, to Levy et al., incorporated herein by reference.

In certain preferred embodiments, the polyvalent cations are associated with only a portion of the substrate. In particular, for tissue heart valves, it may be desirable to only associate the ions with the valve wall, such as the aortic wall for an aortic valve, while leaving the leaflets untreated with the ions. The entire tissue valve preferably would be treated with the VEGF. The treatment of only a portion of a prosthesis with a solution, such as a solution containing polyvalent cations, is described further in copending and commonly assigned U.S. patent application Ser. No. 08/850,812, now U.S. Pat. No. 6,206,917 to Williams et al., entitled "Differential Treatment of Prosthetic Devices," incorporated herein by reference.

Alternatively, the polyvalent ions can be associated with exogenous storage structures which are in turn associated with the substrate. The use of exogenous storage structures for the storage of anticalcification metal ions is described in copending, commonly assigned patent application Ser. Nos. 08/595,402, now U.S. Pat. No. 6,193,749, and 08/690,661, now U.S. Pat. No. 6,302,909, both incorporated herein by reference. Similarly, certain metals such as silver have been associated with antimicrobial activity. Exogenous storage structures can be used to store suitable antimicrobial metal ions in association with a substrate as described in copending and commonly assigned patent application Ser. No. 08/787,139, now U.S. Pat. No. 6,013,106, incorporated herein by reference. Preferred exogenous storage structures include, for example, ferritin and other metal storage proteins. The exogenous storage proteins can be associated with the substrate in ways similar to those used for VEGF. The activities should not interfere with each other.

E. In Vitro Attachment of Endothelial Cells

Growth of viable endothelial cells on prostheses prior to implantation into a patient can be promoted in vitro by joining VEGF with a substrate. In order to reduce the possibility of transplant rejection, the endothelial cells used for in vitro endothelialization preferably are autologous cells, i.e., cells from the ultimate recipient. Suitable cells could be harvested from, for example, adipose tissue of the patient. The harvesting process can involve liposuction followed by collagenase digestion and purification of microvascular endothelial cells. A suitable process is described further in S. K. Williams, "Endothelial Cell Transplantation," Cell Transplantation 4:401-410 (1995), incorporated herein by reference and in U.S. Pat. Nos. 4,883,755, 5,372,945 and 5,628,781, all three incorporated herein by reference. Purified endothelial cells can be suspended in an appropriate growth media such as M199E (e.g., Sigma Cell Culture, St. Louis, Mo.) with the addition of autologous serum.

Prosthetic tissue with bound VEGF can be incubated in a stirred cell suspension for a period of hours to days to allow for endothelial cell seeding. Cell seeding provides random attachment of endothelial cells that can proliferate to coat the surface of the prosthetic substrate either before or after implantation into the patient. Alternatively, the prosthetic substrate can be incubated under a pressure gradient for a period of minutes to promote cell sodding. A suitable method for cell sodding can be adapted from a procedure described for vascular grafts in the S. K. Williams article, supra. Cell sodding can produce a monolayer of cells on the surface of the prosthetic tissue.

In addition, the prosthetic tissue can be placed in a culture system where the patient's endothelial cells are allowed to migrate onto the surface of the prosthetic substrate from adjacent plastic tissue culture surfaces. If either attachment or migration of endothelial cells is performed under conditions involving physiological shear stress, then the endothelial cells colonizing the surface of the substrate may express appropriate adhesion proteins that allow the cells to adhere more tenaciously following implantation.

F. Storage, Packaging, Distribution and Use

Following binding of the VEGF to the substrate, the substrate, possibly formed into a prosthesis, can be stored. The substrate preferably would not have ingrowth of viable cells if the substrate is intended for longer storage. Preferred storage techniques minimize the risk of microbial contamination. For example, the modified substrate can be stored in a sealed container with sterile buffer and/or saline solution.

In a sealed container, the modified substrate is not subjected to a continuous supply of fluids. Nevertheless, consideration should be given to possible loss of VEGF or VEGF activity from the substrate during storage. If excessive loss is a possibility, the storage time can be limited appropriately to keep the loss to an acceptable level.

For distribution, the prostheses generally are placed in sealed and sterile containers. The containers can be dated such that the date reflects the maximum advisable storage time accounting for possible loss or degradation of VEGF activity. The containers are distributed to health care professionals for surgical implantation of the prostheses. In vitro association of cells with a VEGF modified prosthesis preferably is performed at hospitals where the patient's cells can be removed for use in a cell culture system.

As an alternative to the above storage and distribution approach, the VEGF modification can be performed at a hospital or other site separated from the manufacturing site, if desired. Under these circumstances, the prosthesis prepared for VEGF modification is distributed and VEGF association is performed at a later time. Once the prosthesis is modified with VEGF, it can be implanted, stored for a reasonable period of time (up to one month or more) or introduced into a cell culture system to affiliate cells, preferably autologous cells, with the VEGF modified prosthesis.

In certain specific preferred embodiments, the prepared prosthesis, a VEGF solution and a crosslinking solution (if desired) are shipped in separate containers, either as a kit to be used together or as separate articles for use in desired combinations. In particular, the VEGF solution can be shipped with instructions for modifying a substrate with the VEGF. The prosthesis and the solutions are combined immediately prior to use. After the prosthesis has incubated in the solutions for the specified period of time, the prosthesis is removed from the solution, rinsed with a sterile saline solution and implanted into the patient.

Incorporation of VEGF into a prosthesis to promote endothelialization of a substrate should improve biocompatibility of the substrate following implantation. In particular, a quiescent endothelial cell monolayer can serve as a barrier to infection, inflammation, and calcification. Endothelialization of a prosthesis also can promote further recellularization of the prosthesis with cells capable of repairing and remodeling the tissue. Thus, the durability and the longevity of a prosthesis can be significantly improved. Ultimately, recellularization can provide for a prosthesis that more closely resembles a native, biologically competent tissue.

EXAMPLES

Example 1

Direct VEGF Association

This example demonstrates the ability of VEGF to associate with crosslinked tissue and the corresponding effectiveness of VEGF to stimulate affiliation of viable endothelial cells with the tissue.

Several solutions were prepared. The glutaraldehyde solution was prepared in a 5 liter volume by the addition of 19.3 g NaCl, 70.0 g sodium citrate, 2.5 g citric acid, 50 ml of 50% by volume glutaraldehyde (Electron Spectroscopy Sciences, Fort Washington, Pa.), and sufficient reverse osmosis purified water (RO water). A VEGF solution was prepared by diluting 50 µg/ml stock solution of VEGF (human recombinant $VEGF_{165}$, R&D Systems, Minneapolis, Minn.) with 5 ml of 30 mM HEPES buffered saline solution (HBSS, from Clonetics, San Diego, Calif.) for a final concentration of 100 ng/ml. A HEPES buffered saline solution was prepared by adding 17.4 g of NaCl and 35.7 g HEPES free acid to three liters of RO water. An 80% ethanol solution was prepared by combining 1.8 g NaCl, 3.8 g HEPES free acid, 1684 mls of 95% ethanol (Worum Chemical, Saint Paul, Minn., catalog number 200115) and 316 mls of RO water to make 2 liters of solution. All solutions were sterile filtered prior to use.

To prepare the samples, 75 porcine heart valve leaflets were removed from harvested porcine heart valves. The leaflets were stored overnight at 4° C. in 0.9% sterile saline. Then, the leaflets were glutaraldehyde crosslinked in citrate buffered glutaraldehyde solution for a minimum of 6 days. The glutaraldehyde solution was changed twice during the crosslinking procedure, after 24 hours and after three days. The crosslinked leaflets were stored in HEPES buffered glutaraldehyde at room temperature either for 5 days followed by treatment with ethanol (35 leaflets) or for 46 days (40 leaflets).

As stated above, thirty-five leaflets were removed from the glutaraldehyde and were treated with ethanol. Following removal from the glutaraldehyde, these leaflets were incubated in 500 ml of HEPES buffered saline for 10 minutes. This saline was poured off, and the leaflets were incubated in 500 ml of fresh HEPES buffered saline for an additional 15 minutes. After removal of the second saline solution, the leaflets were rinsed once with 80% ethanol and then soaked in 500 ml of 80% ethanol solution for 15 minutes. Then, the first ethanol solution was replaced with an equivalent 500 ml fresh 80% ethanol solution, and the leaflets were incubated in the second ethanol solution for about 24 hours at room temperature.

After 24 hours in ethanol, the leaflets were rinsed with HEPES buffered saline and then soaked in HEPES buffered saline for 15 minutes. After changing the solution, the leaflets were soaked in HEPES buffered saline for 24 hours. The leaflets were then transferred to a storage container containing HEPES buffered saline. The leaflets in the storage container were subjected to gamma sterilization by SteriGenics (Charlotte, S.C.). Gamma irradiation caused the leaflets in HEPES buffered saline to turn brown. Following sterilization, the leaflets were stored in this container at 4° C. until further use.

Both ethanol treated and non-ethanol treated glutaraldehyde crosslinked leaflets were removed from storage and cut in half. The cut leaflets were rinsed three times with 100 ml of 0.9% sterile saline. Following the rinses, six of the ethanol treated and six of the non-ethanol treated leaflet halves were incubated in HBSS containing 100 ng/ml VEGF. Leaflets were incubated in the VEGF solution overnight at 4° C.

Four six-well plates were prepared with 2% gelatin (Sigma Chemical, St. Louis, Mo.) and EGM media (Clonetics, San Diego, Calif.) to support cell growth. Human umbilical vein endothelial cells (HUVECs) from Clonetics (lot #2803) were grown to confluence in each of the 24 wells. Twenty four hours after achieving confluence, a sterilized rubber policeman was used to scrape the cells from the center of each well. Media containing the cellular debris was removed and replaced with fresh EGM media. Each well was examined by light microscopy to assure that cells have been removed from the center of each well.

Leaflet halves were placed in the scraped clear center of each plate, and either normal EGM media or EGM media containing 10 ng/ml VEGF was added according to the following protocol:
1) No leaflet, media without VEGF (3 wells);
2) No leaflet, media with VEGF (3 wells);
3) Ethanol treated leaflet, media without VEGF (4 wells);
4) Ethanol treated leaflet, media with VEGF (4 wells);
5) Ethanol and VEGF treated leaflet, media without VEGF (4 wells);
6) Non-ethanol treated leaflet, media without VEGF (2 wells); and
7) VEGF treated, non-ethanol treated leaflet, media without VEGF (4 wells).

Leaflet halves that were not pretreated with VEGF were rinsed three times with sterile saline, as described previously. The VEGF pretreated leaflets had been rinsed before treatment with VEGF and did not receive any additional rinses before placement into a well.

A fifth six-well plate was used in which HUVECs were cultured onto the top membrane of tissue culture inserts that were placed inside each well. Once the cells on this membrane had achieved confluence, a hole was cut in the center of each insert membrane using a sterile scalpel. A leaflet was placed on the bottom of each well, and the insert was placed over the leaflet such that the edges of the hole in the insert membrane rested on the leaflet. Each well was filled with 2 mls of EGM media. On this plate, two of the leaflets were ethanol treated with no VEGF treatment, two leaflets had ethanol treatment followed by VEGF treatment and two leaflets had VEGF treatments but no ethanol treatment.

After about five hours, the media in all the wells of the five plates was replaced. The cells then were allowed to grow for a total of about five days with fresh media added every other day. After four days, all wells were examined using a light microscope. Since the leaflets are opaque, this technique did not allow for visualization of cells attached to the leaflets. It was also impossible to see cells grown on top of the inserts since these membranes were also opaque. Given these limitations, the following observations were made:
1) Cells grown in wells containing no leaflets had resumed growth to cover the area scraped clear and were again almost confluent;
2) Most of the cells in the wells containing glutaraldehyde leaflets with no further treatments were dead; and
3) Ethanol treated leaflets did not appear to be cytotoxic.

After five days, half of the tissue samples were rinsed twice with Dulbecco's phosphate buffered saline (Gibco BRL, Grand Island, N.Y.). The rinsed samples were fixed with 3% formaldehyde solution for at least five minutes. The fixed samples were rinsed three times with RO water and once with 0.25M sucrose.

A 5 mM stock solution of a fluorescent, lipophilic probe, dioctadecyl tetramethyl indocarbocyanine perchlorate (DiI) from Molecular Probes Inc., Eugene, Oreg. (catalog No. D-282) was prepared by adding 0.00467 grams of DiI powder to 1 ml of dimethyl sulfate (DMS) in a 1.5 ml microcentrifuge tube. DiI is a cell membrane stain. The tube was vortexed to dissolve the powder. The tube was stored at room temperature wrapped in aluminum foil and kept away from light sources. A 50 μM solution of DiI was prepared by adding 150 μl of the 5 mM stock solution to 15 mls of 0.25M sucrose solution in a centrifuge tube. The tube was vortexed to mix the solution. The dilute DiI solution was made fresh on the day of use.

The tissue samples were fluorescently stained by covering each rinsed leaflet in its well with sufficient 50 μM DiI solution. The plates were covered with aluminum foil to avoid light exposure. The leaflets were stained for at least about 15 minutes but no more than about 25 minutes. Then, the samples were rinsed four times with RO water. Following rinsing, 0.9% saline was added to each sample to prevent it from drying out, and the samples were covered with aluminum foil to prevent bleaching prior to examination. The stained tissue samples were imaged using a tetramethylrhodamine isothiocyanate (TRITC) filter and photographed.

Figure 2:
FIG. 2 is a micrograph of a crosslinked tissue sample that was treated with VEGF prior to a five day incubation with endothelial cells in a tissue culture well. In this example, the tissue treated with VEGF was not in direct contact with endothelial cells at the start of the incubation period. Endothelial cells present on the fixed tissue are visualized by fluorescent labeling.

No cells grew on the ethanol treated leaflets, and no cells grew on the untreated leaflets except for a few cells growing on one sample in contact with a membrane insert. Similarly, 10 ng/ml VEGF in solution did not stimulate the affiliation of cells with the tissue. Only background fluorescence was observed with leaflets lacking cells when examined through the TRITC filter. Leaflets with VEGF adsorbed to the surface had colonies of brightly fluorescent cells attached to the leaflets indicating stimulation of endothelial cell migration toward the leaflet and of adherence to the leaflet. This can be seen in FIG. 1 for a representative leaflet in direct contact with endothelial cells on a membrane insert and in FIG. 2 for a representative leaflet placed in a section of a well initially clear of endothelial cells. The use of an insert did not qualitatively alter the results.

Similar results were seen in other experiments where glutaraldehyde crosslinked leaflets were incubated in 100 ng/ml VEGF. In particular, VEGF enhanced both HUVEC and human aortic endothelial cell colonization of the leaflets over a period of five to thirty days in culture. Additional experiments also showed that VEGF was most effective when it was adhered to leaflets that had been stored in HEPES buffered glutaraldehyde solution for less than one month prior to incubation with VEGF.

Example 2

Glutaraldehyde Crosslinking of VEGF to Ethanol Treated Crosslinked Tissue

This example demonstrates that a low concentration glutaraldehyde solution effectively crosslinks VEGF to ethanol treated glutaraldehyde crosslinked tissue without loss of the ability of VEGF to stimulate endothelial cell proliferation and chemotaxis.

All solutions were prepared fresh on the day of use and were filtered through a 0.25 μm filter. A HEPES buffered saline solution consisted of 0.1M NaCl and 50 mM HEPES in reverse osmosis purified water (RO water). The pH of the HEPES buffered saline solution was adjusted to 7.4. A 0.01% glutaraldehyde solution was prepared by adding 20 μl of a 50% by volume stock solution of glutaraldehyde (Electron Microscopy Sciences, Fort Washington, Pa.) to 100 ml of HEPES buffered saline. A VEGF/glutaraldehyde solution was prepared by adding 2 μg VEGF (human recombinant $VEGF_{165}$, R&D Systems, Minneapolis, Minn.) to 20 ml of the 0.01% glutaraldehyde solution, resulting in a solution with 100 ng/ml VEGF and 0.01% glutaraldehyde.

Eight glutaraldehyde crosslinked and ethanol treated leaflets were prepared as described in Example 1 and rinsed with sterile saline. Three leaflets were incubated in the VEGF/glutaraldehyde solution for 15 minutes and three leaflets were incubated in the VEGF/glutaraldehyde solution for 30 minutes. The remaining two leaflets were stored in HEPES buffered saline to be used as controls. After the incubation periods were over, the leaflets were rinsed three times in sterile 0.9% saline for two minutes per rinse.

Several days prior to incubation of the treated leaflets, two six-well tissue culture plates coated with 2% gelatin were seeded with human aortic endothelial cells (Clonetics, San Diego, Calif.). The endothelial cells were grown to confluence, with fresh endothelial growth media (EGM) (Clonetics, San Diego, Calif.) added every other day. Prior to the addition of the tissue sample to the tissue culture plates, the center section of each tissue culture well was scraped clean of endothelial cells. Each well was rinsed two times with EGM to remove cellular debris.

Immediately following the VEGF incubation and rinsing of the leaflets, the leaflets were placed in the cleared portion of the wells, one leaflet per well. Sterile tissue culture inserts (Sigma Chemical Co., St. Louis, Mo.) were placed over the leaflets to prevent them from floating. Fresh EGM was added to the wells every other day. After five days, the leaflets were placed in 3% formaldehyde to fix any cells that had adhered to the surface of the leaflets. The leaflets then were stained with a fluorescent lipophilic probe, dioctadecyl tetramethyl indocarbocyanine perchlorate (Molecular Probes, Eugene, Oreg.), as described in Example 1.

Figure 3:
FIG. 3 is a set of micrographs of tissue samples following incubation with endothelial cells in a cell culture system, where the tissue was treated only with ethanol (FIG. 3A), or where the crosslinked ethanol treated tissue was treated for fifteen minutes with a VEGF/glutaraldehyde solution (FIG. 3B) or for thirty minutes with a VEGF/glutaraldehyde solution (Fig. C). The cells were visualized by fluorescent labeling.

The stained samples were imaged using a tetramethylrhodamine isothiocyanate filter and photographed. The leaflets incubated for either 15 minutes (FIG. 3B) or 30 minutes (FIG. 3C) in the VEGF/glutaraldehyde solution had significant numbers of endothelial cells colonizing the surface of the leaflets, as compared to control leaflets (FIG. 3A). Thus, use of 0.01% glutaraldehyde to crosslink VEGF to the surface of an ethanol treated leaflet did not appear to be cytotoxic to endothelial cells colonizing that leaflet. Additionally, VEGF was effective at promoting endothelial cell colonization of the treated tissue. It is significant that the ethanol treatment of the leaflets did not prevent the binding of VEGF under these circumstances since ethanol treatment of glutaraldehyde crosslinked tissue has been previously shown to improve biocompatibility and to inhibit calcification of the tissue following implantation.

Figure 5:
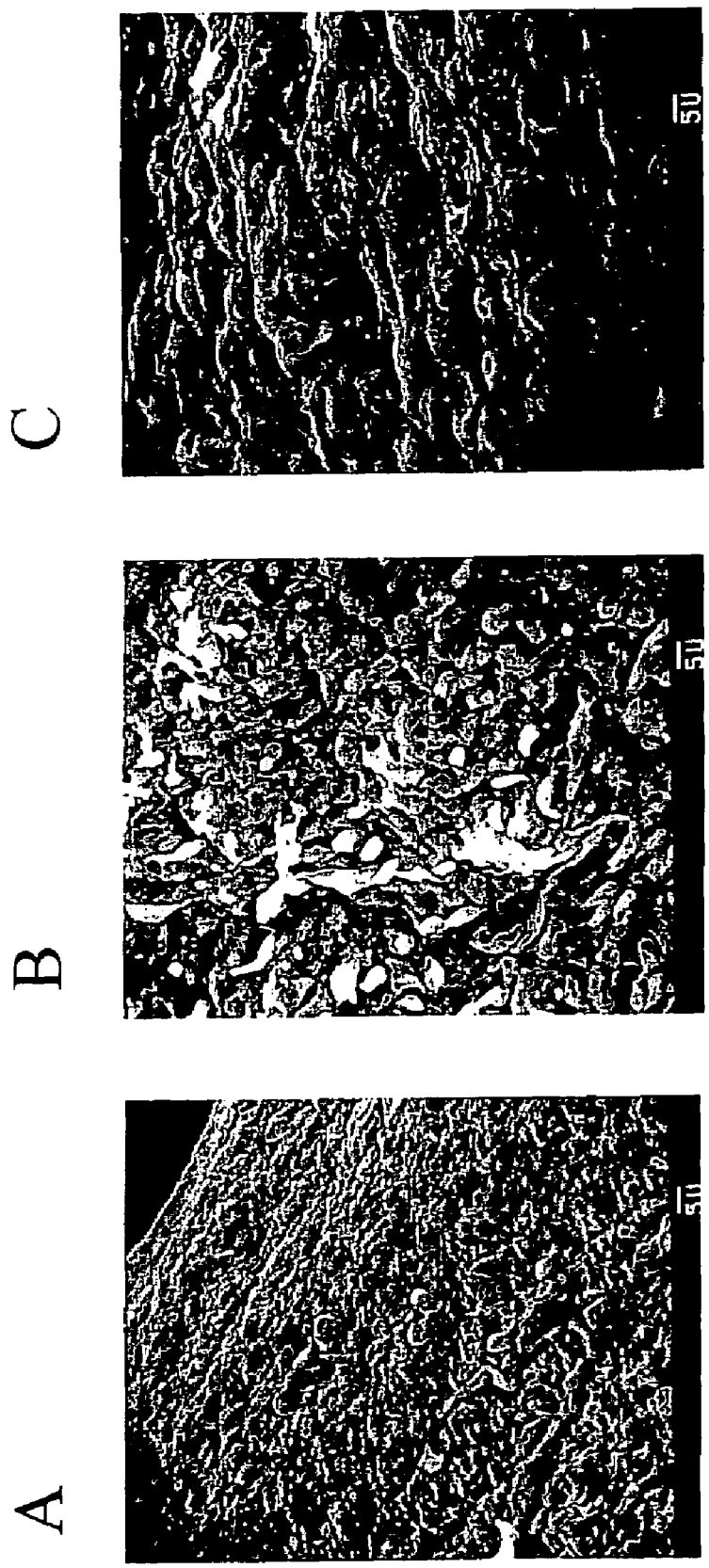
FIG. 5 is a set of micrographs of human aortic endothelial cells colonizing glutaraldehyde crosslinked porcine aortic valve leaflet tissue (FIG. 5A), glutaraldehyde crosslinked tissue treated with ethanol (FIG. 5B), or glutaraldehyde crosslinked tissue treated with ethanol and then with a solution of 100 ng/ml VEGF+0.01% glutaraldehyde. The cells were visualized by scanning electron microscopy.

Similar results were seen in other experiments in which in vitro assays were used to compare the ability of human aortic endothelial cells to colonize untreated or treated glutaraldehyde crosslinked tissue. Glutaraldehyde crosslinked tissue without ethanol or VEGF treatment was a poor substrate for human endothelial cell growth, as shown in FIGS. 4A and 5A. The micrographs shown in FIG. 4 were obtained after fixing cells adhered to the tissue with 3% formalin and fluorescent staining. The micrographs shown in FIG. 5 were obtained after fixing cells adhered to the tissue with phosphate buffered, 2% glutaraldehyde solution for at least 24 hours. Then, the tissue was serially dehydrated with ethanol and with a final dehydration with hexamethyldisilizane. Samples were attached to SEM stubs, and coated with gold palladium. The tissue samples were imaged using an Hitachi™ 450 Scanning Electron Microscope.

Incubation of glutaraldehyde crosslinked tissue in 80% ethanol, as described in Example 1, improves biocompatibility, such that the ethanol treated tissue supports larger colonies of endothelial cells, as shown in FIGS. 4B and 5B. Scanning electron micrographs of these sample show, however, that the endothelial cells adhering to ethanol treated tissue have a round morphology characteristic of loosely adhered or dying cells (FIG. 5B). If the ethanol treated leaflets undergo an additional 30 minute incubation in a solution of 100 ng/ml VEGF/0.01% glutaraldehyde, as described above, the VEGF treated tissue is capable of more rapid and complete endothelialization, as shown in FIGS. 4C and 5C. In contrast with the cells seen in the other treatment groups, scanning electron micrographs show that endothelial cells adhering to the VEGF treated tissue are considerably more spread (FIG. 5C). This spread morphology is indicative of a healthier endothelial cell lining.

Example 3

Glutaraldehyde Crosslinking of VEGF to Fresh Tissue

This example demonstrates that a low concentration (0.01%) glutaraldehyde solution can be used to attach VEGF to fresh porcine aortic leaflet tissue without loss of the ability of VEGF to stimulate endothelial cell proliferation and chemotaxis.

A HEPES buffered saline solution, a 0.01% glutaraldehyde solution and a VEGF/glutaraldehyde solution were prepared as described in Example 2. Six porcine aortic leaflets were harvested using sterile surgical technique and rinsed in 0.9% sterile saline. Two of the leaflets were incubated in 10 ml HEPES buffered saline solution. Two other leaflets were incubated in 10 ml 0.01% glutaraldehyde solution. The remaining two leaflets were incubated in 10 ml VEGF/glutaraldehyde solution. All leaflets were incubated in their respective solutions for 30 minutes. At the end of the 30 minute incubation period, the leaflets were rinsed three times in 100 ml of 0.9% sterile saline solution. Each rinse was performed for two minutes.

Several days prior to treatment of the leaflets, a six-well tissue culture plate coated with 2% gelatin was seeded with human aortic endothelial cells (Clonetics, San Diego, Calif.). The endothelial cells were allowed to grow to confluence and fresh EGM (Clonetics, San Diego, Calif.) was added to the wells every other day. During the 30 minute incubation period for the leaflets, the center section of each tissue culture well was scraped clear of endothelial cells. The wells then were rinsed with fresh EGM to remove cellular debris. Immediately, following the 30 minute incubation period and subsequent rinses, one leaflet was placed in the cleared portion of each tissue culture well. Sterile tissue culture inserts (Sigma Chemical Co., St. Louis, Mo.) were placed over the leaflets to prevent them from floating. Fresh EGM was added, and the tissue culture plate was returned to a tissue culture incubator.

Fresh EGM was added to the wells every other day. The incubation was continued for five days. At the end of the five day period, cells adhered to the surface of the leaflets were fixed with 3% formaldehyde. The leaflets then were stained with a fluorescent lipophilic probe, dioctadecyl tetramethyl indocarbocyanine perchlorate (Molecular Probes, Eugene, Oreg.), as described in Example 1.

Figure 6:
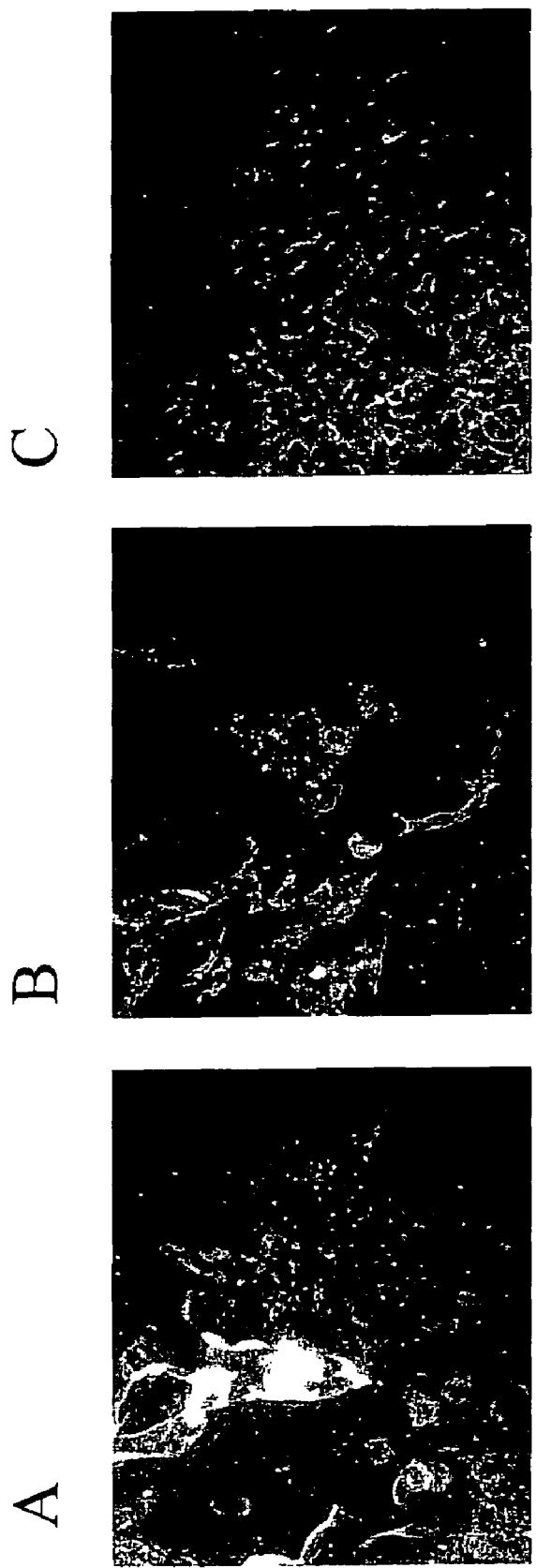
FIG. 6 is a set of micrographs of human aortic endothelial cells colonizing uncrosslinked porcine aortic valve leaflet tissue previously incubated in a HEPES buffered saline solution (FIG. 6A), in a HEPES buffered saline/0.01% glutaraldehyde solution (FIG. 6B) or in a HEPES/0.01% glutaraldehyde/100 ng per ml VEGF solution (FIG. 6 C). The cells were visualized by fluorescent labeling.

The stained tissue samples were imaged using a tetramethyl rhodamine isothiocyanate filter and photographed. The photographs are shown in FIGS. 6A-6C. Some colonies of endothelial cells were observed on tissue that had been incubated in either HEPES buffered saline or in 0.01% glutaraldehyde. Leaflets incubated in the VEGF/glutaraldehyde solution had many more endothelial cells colonizing the tissue, as seen by comparing FIG. 6C with FIGS. 6A and 6B. Thus, incubation in a buffered solution of 0.01% glutaraldehyde containing 100 ng/ml VEGF had no negative effect on human aortic endothelial cell survival and accelerated endothelial cell coverage of porcine aortic tissue.

Example 4

VEGF Induced Inhibition of Leaflet Calcification

This example demonstrates that a combined treatment of glutaraldehyde crosslinked porcine aortic valve leaflets with both VEGF and ethanol can inhibit calcification of those leaflets, as evaluated in a juvenile rat subcutaneous implant model.

A juvenile rat subcutaneous implant model has been shown to closely mimic clinically relevant heart valve calcification (Levy et al., Am. J. Pathol. 113:143-155 (1983)). Therefore, the model is used to evaluate calcification potential of leaflets subjected to various processes or surface modifications.

The preparation of all solutions and the treatment of leaflets in these solutions was performed as described in detail in Examples 1 and 2. Briefly, 45 leaflets were harvested from porcine aortic valves and crosslinked in 0.5% citrate buffered glutaraldehyde. Fifteen of these leaflets (the Control Group) were stored in HEPES buffered saline until immediately prior to implantation. The remaining 30 leaflets were incubated in an 80% ethanol solution for 24 hours and then subjected to sterilization by gamma irradiation. During and after gamma irradiation, the leaflets were stored in HEPES buffered saline. Fifteen of the ethanol treated leaflets (the Ethanol and VEGF Group) were incubated in a solution of 0.01% glutaraldehyde/ 100 ng/ml VEGF solution for thirty minutes on the day of implantation.

Prior to implantation, all leaflets were rinsed three times in 100 ml of sterile 0.9% saline for about two minutes per rinse. Using aseptic technique, leaflets were then coded with sterile colored suture to differentiate leaflets from each of the three groups (white=Control Group, green=Ethanol Group, black=Ethanol and VEGF Group). Coded leaflets were stored in sterile saline and transported to the Ramsey Animal Laboratory at Regions Hospital in Saint Paul, Minn., where the subcutaneous implantation was performed.

Surgical procedures were performed under aseptic conditions. Three week old male Sprague-Dawley rats were anesthetized by interperitoneal injection of ketamine hydrochloride and four subcutaneous pouches at least 2 cm in diameter were dissected in the midabdominal wall of each rat. Four leaflets were implanted in the subcutaneous pouches of each rat, one leaflet per pouch. Every rat received at least one, but no more than two leaflets from each treatment group. Wounds were closed with surgical staples, and rats were allowed to recover. Leaflets were implanted for either 21 days (10 leaflets in each treatment group) or 63 days (5 for each treatment group). At the end of the implantation period, the samples were recovered from the rats. The recovered samples were stored in sterile saline and transported for analysis.

Each tissue sample was sectioned in half along the radial axis. One half of the tissue sample was cleaned of host tissue that results from encapsulation response during implantation and dehydrated. The dehydrated samples were subjected to inductively coupled plasma atomic emission spectroscopy (ICP-AES) for determination of the calcium content. The second half of each tissue sample was placed in 10% formalin and forwarded to American Histo Labs (Gaithersburg, Md.) for histological sample preparation utilizing von Kossa's stain to specifically stain calcium phosphate crystals.

Figure 7:
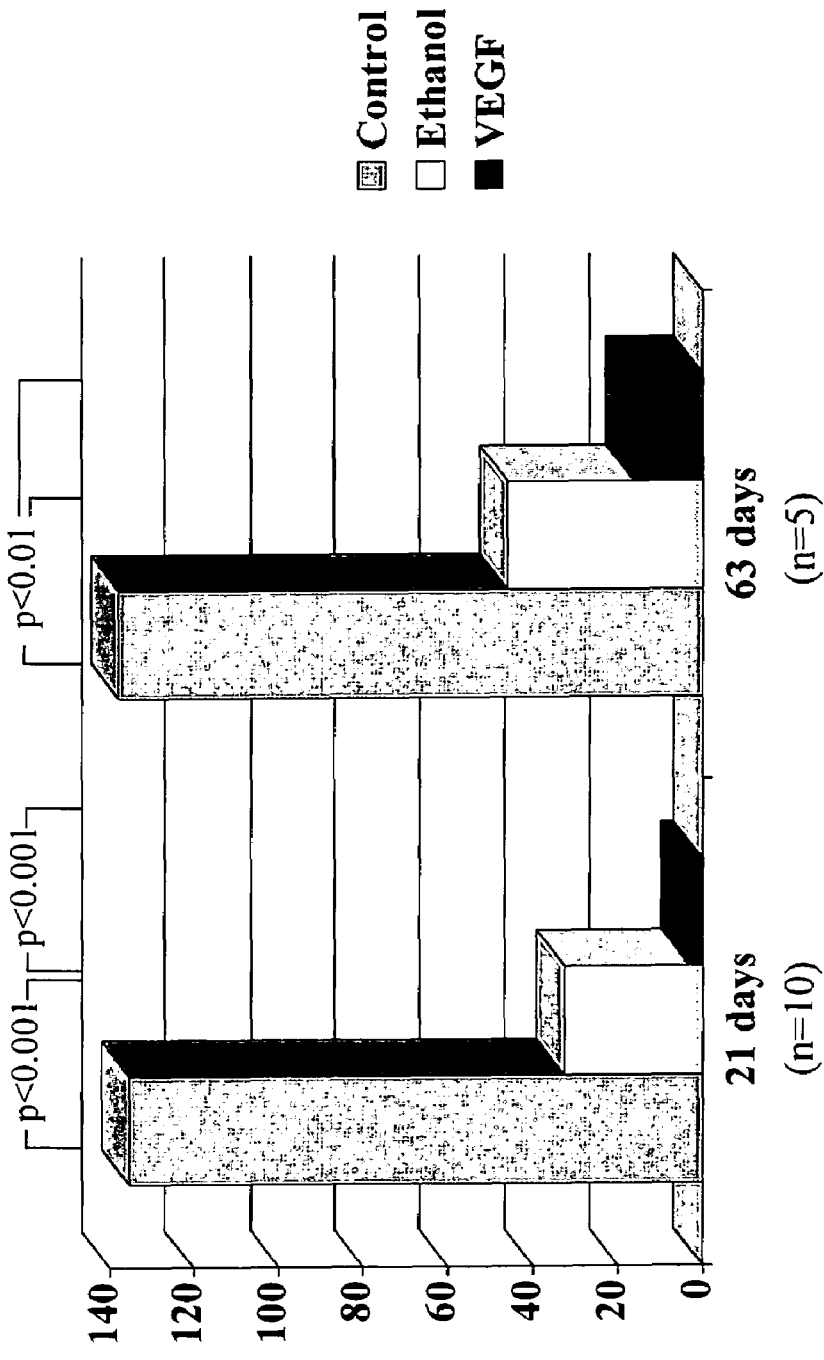
FIG. 7 is a graphical representation of the calcium content in glutaraldehyde crosslinked leaflets that received no further treatment (control), ethanol treatment (ethanol) or ethanol and VEGF treatment (VEGF) prior to subcutaneous implantation in juvenile male rats for either 21 or 63 days.

FIG. 7 is a plot of the average results from the ICP-AES assay for calcium content. Ethanol treatment significantly inhibited calcification at both 21 and 63 days. The addition of VEGF to ethanol treatment further attenuated calcification. FIG. 8 shows representative photographs from the histological analysis of tissue samples for calcium phosphate using von Kossa's stain. The photographs in FIG. 8 confirm the inhibition of calcification by ethanol and the synergistic inhibition of calcification by the ethanol/VEGF combination.

The embodiments described above are intended to be illustrative and not limiting. Additional embodiments are within the claims. Although the present invention has been described with reference to preferred embodiments, workers skilled in the art will recognize that changes may be made in form and detail without departing from the spirit and scope of the invention.

What is claimed is:

1. A biomedical device comprising a natural tissue and a polypeptide growth factor associated with the natural tissue by covalent bonding using crosslinking agents, antibody-antigen associations, specific binding protein-receptor associations or enzyme-substrate associations, wherein the crosslinking agents comprise at least two aldehyde functional groups that form covalent bonds to link the crosslinking agent directly with the polypeptide growth factor and the natural tissue, the polypeptide growth factor associated with the natural tissue being effective to stimulate association of viable cells with the substrate.

2. The biomedical device of claim 1 wherein the crosslinking agent comprises difunctional aldehydes.

3. The biomedical device of claim 2 wherein the difunctional aldehyde comprises glutaraldehyde.

4. The biomedical device of claim 1 wherein the natural tissue comprises xenograft or homograft tissue.

5. The biomedical device of claim 1 wherein the natural tissue comprises human tissue.

6. The biomedical device of claim 1 wherein the natural tissue is selected from the group consisting of porcine tissue, bovine tissue, kangaroo tissue, canine tissue and a combination thereof.

7. The biomedical device of claim 1 wherein the polypeptide growth factor comprises vascular endothelial growth factor.

8. The biomedical device of claim 1 wherein the polypeptide growth factor comprises Tat protein.

9. The biomedical device of claim 1 wherein the biomedical device comprises an artificial organ, a heart valve prosthesis, an annuloplasty ring, a stent, a pledget, suture, an electrical lead, a permanently in-dwelling percutaneous device, an AV shunt, a vascular graft, a dermal graft or a surgical patch.

10. A biomedical device comprising a biocompatible substrate and a polypeptide growth factor associated with the biocompatible substrate, the polypeptide growth factor being effective to stimulate association of viable cells with the substrate, wherein the polypeptide growth factor comprises Tat protein.

11. The biomedical device of claim 10 wherein the biocompatible substrate comprises tissue.

12. The biomedical device of claim 10 further comprising an adhesive, the adhesive being associated with the polypeptide growth factor and the substrate.

13. A biomedical device comprising a substrate and a polypeptide growth factor associated with the substrate by antibody-antigen associations, specific binding protein-receptor associations or enzyme-substrate associations, the polypeptide growth factor associated with the substrate being effective to stimulate association of viable cells with the substrate.

14. The biomedical device of claim 13 wherein the biocompatible substrate comprises tissue.

15. The biomedical device of claim 13 wherein the biocompatible substrate comprises a synthetic material.

16. The biomedical device of claim 13 wherein the substrate comprises a bioresorbable material.

17. The biomedical device of claim 13 wherein the polypeptide growth factor is associated with the substrate by antibody-antigen associations.

18. The biomedical device of claim 13 wherein the polypeptide growth factor is associated with the substrate by specific binding protein-receptor associations.

19. The biomedical device of claim 13 wherein the polypeptide growth factor is associated with the substrate by enzyme-substrate associations.

20. A prosthesis comprising:
a substrate of the prosthesis; and
a polypeptide growth factor associated with the substrate, the polypeptide growth factor being effective to stimulate association of viable cells with the substrate,
wherein said polypeptide growth factor comprises Tat protein.

21. The prosthesis of claim 20 further comprising an adhesive, the adhesive being associated with the polypeptide growth factor and the substrate.

22. The biomedical device of claim 10 further comprising a crosslinking agent, said crosslinking agent associating the growth factor to the biocompatible substrate.

23. A prosthesis comprising a substrate and a polypeptide growth factor associated with the substrate, the polypeptide growth factor being effective to stimulate association of viable cells with the substrate, said polypeptide growth factor comprising Tat protein, said polypeptide growth factor is associated with the substrate by covalent bonding using crosslinking agents, antibody-antigen associations, specific binding protein-receptor associations, enzyme-substrate associations, or an adhesive.

24. A biomedical device comprising a biological matrix and a polypeptide growth factor crosslinked to the biological matrix by covalent bonding using crosslinking agents, wherein the crosslinking agents comprise at least two aldehyde functional groups that form covalent bonds to link the crosslinking agent directly with the polypeptide growth factor and the biological matrix, the polypeptide growth factor associated with the biological matrix being effective to stimulate association of viable cells with the substrate.

* * * * *